US008916156B2

(12) United States Patent
Mason

(10) Patent No.: US 8,916,156 B2
(45) Date of Patent: *Dec. 23, 2014

(54) ISOLATED EGG PROTEIN AND EGG LIPID MATERIALS, AND METHODS FOR PRODUCING THE SAME

(71) Applicant: Rembrandt Enterprises, Inc., Rembrandt, IA (US)

(72) Inventor: David Mason, North Vancouver (CA)

(73) Assignee: Rembrandt Enterprises, Inc., Rembrandt, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/070,120

(22) Filed: Nov. 21, 2013

(65) Prior Publication Data

US 2014/0066596 A1 Mar. 6, 2014

Related U.S. Application Data

(63) Continuation-in-part of application No. 12/910,780, filed on Oct. 22, 2010, now Pat. No. 8,642,038, and a continuation-in-part of application No. 13/481,075, filed on May 25, 2012.

(60) Provisional application No. 61/361,197, filed on Jul. 2, 2010, provisional application No. 61/491,163, filed on May 27, 2011.

(51) Int. Cl.
| *A61K 39/00* | (2006.01) |
| *A01K 43/04* | (2006.01) |
| *C07K 1/34* | (2006.01) |
| *C07K 14/77* | (2006.01) |
| *A23L 1/32* | (2006.01) |
| *A23J 1/09* | (2006.01) |
| *A23J 3/00* | (2006.01) |

(52) U.S. Cl.
CPC . *C07K 1/34* (2013.01); *C07K 14/77* (2013.01); *A23L 1/32* (2013.01); *A23J 1/09* (2013.01); *A23J 3/04* (2013.01); *A23V 2002/00* (2013.01)
USPC ........................................ 424/157.1; 209/510

(58) Field of Classification Search
None
See application file for complete search history.

(56) References Cited

U.S. PATENT DOCUMENTS

| 2,377,961 | A | 6/1945 | Pollak |
| 2,451,116 | A | 10/1948 | Pollak |
| 3,950,557 | A | 4/1976 | Kheng |
| 4,034,124 | A | 7/1977 | Van Dam |
| 4,330,446 | A | 5/1982 | Miyosawa |
| 4,364,966 | A | 12/1982 | Chang |
| 4,552,845 | A | 11/1985 | Reid |
| 4,612,197 | A | 9/1986 | Postner |
| 4,721,674 | A | 1/1988 | Lepienne et al. |
| 4,814,111 | A | 3/1989 | Kearns et al. |
| 4,847,015 | A | 7/1989 | Shigematsu et al. |
| 4,986,918 | A | 1/1991 | Breslau et al. |
| 5,028,447 | A | 7/1991 | Schenk |
| 5,302,405 | A | 4/1994 | Hsieh et al. |
| 5,367,054 | A | 11/1994 | Lee |
| 5,399,331 | A | 3/1995 | Loughrey et al. |
| 5,468,844 | A | 11/1995 | Smith |
| 5,487,912 | A | 1/1996 | Meibach et al. |
| 5,716,526 | A | 2/1998 | Kelemen et al. |
| 5,932,250 | A | 8/1999 | Stolle et al. |
| 5,945,149 | A | 8/1999 | Andreae et al. |
| 6,174,443 | B1 | 1/2001 | Ruckenstein et al. |
| 6,217,926 | B1 | 4/2001 | Merkle et al. |
| 6,773,731 | B2 | 8/2004 | Campbell |
| 6,863,908 | B2 | 3/2005 | Hamm et al. |
| 7,166,223 | B2 | 1/2007 | Bomberger et al. |
| 7,297,261 | B2 | 11/2007 | Bomberger et al. |
| 7,297,262 | B2 | 11/2007 | Bomberger et al. |
| 7,338,553 | B2 | 3/2008 | Foster |
| 7,368,215 | B2 | 5/2008 | Munnelly et al. |
| 7,402,246 | B2 | 7/2008 | Bomberger et al. |
| 7,566,570 | B2 | 7/2009 | Abril |
| 8,642,038 | B2 | 2/2014 | Mason |
| 2004/0029164 | A1 | 2/2004 | Ransohoff |
| 2004/0081725 | A1 | 4/2004 | Lee |
| 2006/0223986 | A1 | 10/2006 | Chiou |
| 2007/0017447 | A1 | 1/2007 | Vlad |
| 2007/0259096 | A1 | 11/2007 | Qi et al. |
| 2008/0071067 | A1 | 3/2008 | Chen et al. |
| 2008/0096813 | A1 | 4/2008 | Frankel et al. |
| 2008/0166447 | A1 | 7/2008 | Strohbehn et al. |

(Continued)

FOREIGN PATENT DOCUMENTS

| EP | 0737425 | 10/1996 |
| GB | 1525929 | 9/1978 |
| WO | 2005099487 | 10/2005 |
| WO | 2008086431 | 7/2008 |
| WO | 2012003322 A2 | 1/2012 |

OTHER PUBLICATIONS

Ahn et al., "Sequential Separation of Main Components from Chicken Egg Yolk", Food Sci. Biotechnol., vol. 15, No. 2, pp. 189-195, (2006). Awade et al., "Two-Step Chromatographic Procedure for the Purification of Hen Egg White Ovomucin, Lysozyme, Ovotransferrin and Ovalbumin and Characterization of Purified Proteins", J. Chromatogr. A 1994, 677:279-288.

Chiang B. H., "Egg White Lysozyme Purification by Ultrafiltration and Affinity Chromatography", Journal of Food Science Mar. 1993, 58:2, pp. 303-306.

(Continued)

*Primary Examiner* — Thane Underdahl
(74) *Attorney, Agent, or Firm* — Pauly, Devries Smith & Deffner, LLC

(57) ABSTRACT

A method for separating proteins and fats from an egg mixture is disclosed herein. The method includes a step of microfiltration of the egg mixture, wherein microfiltration includes pumping across a filter an egg mixture containing egg yolk and egg whites (albumen). An egg powder obtained from egg and a high gel strength egg powder are also disclosed.

20 Claims, 2 Drawing Sheets

(56) References Cited

U.S. PATENT DOCUMENTS

| | | |
|---|---|---|
| 2008/0206436 A1 | 8/2008 | Strohbehn et al. |
| 2008/0268124 A1 | 10/2008 | Campbell et al. |
| 2009/0104173 A1 | 4/2009 | Strohbehn et al. |
| 2009/0274770 A1 | 11/2009 | Gammelsaeter et al. |
| 2010/0029564 A1 | 2/2010 | Strohbehn et al. |
| 2010/0175570 A1 | 7/2010 | Vlad |
| 2011/0033440 A1 | 2/2011 | Strohbehn et al. |
| 2011/0034401 A1 | 2/2011 | Strohbehn et al. |
| 2012/0004399 A1 | 1/2012 | Mason |

OTHER PUBLICATIONS

Lu, Junren, "Fractionation of Lysozyme and Chicken Egg Albumin Using Ultrafiltration with 30-kDa Commercial Membranes", Ind. Eng. Chem. Res. 2005, 44(20), pp. 7610-7616.

Song et al., "Study on Seperation and Purification of Immunoglobulin in Yolk," Food Science, vol. 26, Issue (4): 51-54, 1 page abstract, 2005.

Wagner, "Membrane Filtration Handbook", Second Edition, Revision 2, Nov. 2001, 129 pages.

First Office Action for Chinese Patent Application No. 201180029076.1, mailed Sep. 29, 2013, English translation, 19 pages.

International Preliminary Report on Patentability for PCT/US2011/042603, mailed Jan. 17, 2013, (10 pages).

Non-Final Office Action, mailed Jan. 23, 2013, in co-pending U.S. Appl. No. 12/910,780, (21 pages).

Notice of Allowance from U.S. Appl. No. 12/910,780, mailed Aug. 2, 2013, 13 pages.

PCT International Search Report and Written Opinion from International Application No. PCT/US2011/042603, mailed Feb. 24, 2012, 16 pages.

PCT Notification Concerning Transmittal of International Preliminary Report on Patentability from International Application No. PCT/US2011/042603, mailed Jan. 17, 2013, 11 pages.

US 8,916,156 B2

ISOLATED EGG PROTEIN AND EGG LIPID MATERIALS, AND METHODS FOR PRODUCING THE SAME

This application is a continuation-in-part application of U.S. application Ser. No. 12/910,780, filed Oct. 22, 2010, which claims the benefit of U.S. Provisional Application Ser. No. 61/361,197, filed Jul. 2, 2010; and a continuation-in-part application of U.S. application Ser. No. 13/481,075, filed May 25, 2012, which claims the benefit of U.S. Provisional Application No. 61/491,163, filed May 27, 2011. The entire contents of each of these U.S. Applications are incorporated herein by reference.

FIELD OF THE INVENTION

The invention described herein relates to processing of eggs and, in particular, processes that separate proteins and fats from eggs, as well as materials produced by the separation processes.

BACKGROUND OF THE INVENTION

Chicken eggs are one of the most important foods in the human diet, and are an exceptional source of proteins and fats, as well as amino acids and fatty acids. Every year in the United States an estimated 90 billion eggs are produced, with three fourths of these eggs being used for human consumption. An estimated 250 eggs per person are consumed annually in the United States.

Many of the eggs consumed by humans are eaten as food ingredients, rather than directly as cooked eggs (such as boiled, fried, poached, etc.). In some cases whole eggs are used as food ingredients, for example as baking applications. However, it is often desirable to use just a portion of an egg as a food ingredient. For example, egg yolk is an excellent emulsifier and surfactant, and is an essential component of mayonnaise and various other foods. The egg yolk makes up approximately one third of the liquid weight of an egg, and is high in fats and fatty acids. Important fat soluble vitamins (A, D, E, and K) are found in egg yolk, as are unsaturated fatty acids (e.g. oleic acid, linoleic acid, palmitoleic acid, and linolenic acid) and saturated fatty acids (e.g. palmitic acid, stearic acid, and myristic acid). Egg yolks also contain some proteins, typically on the order of 2 to 3 grams out of about 15 to 20 grams of yolk within an egg weighing approximately 50 grams.

The egg white, known as well as the albumen, also has unique uses as a result of having high protein content. Egg whites are used in many products, such as to make mousse and to enhance protein content of foods. Egg white is approximately two-thirds of the total weight of an egg, with approximately 90 percent of that weight coming from water. The remaining weight of the egg white comes primarily from protein, along with various trace minerals, vitamins, some fats, and glucose. A typical large egg may contain 35 to 40 grams of egg white, of which about 4 to 5 grams are proteins. The most common protein in egg whites is ovalbumen, which accounts for over half of the proteins. Ovotransferrin and ovomucoid are additional primary proteins, with other proteins including ovoglobulin G2, Ovoglobulin G3, ovomucin, lysozyme, ovoinhibitor, ovoglycoprotein, flavoprotein, ovomacroglbulin, avidin, and crystatin. The egg white contains no dietary cholesterol, but does contain small quantities of other lipids and fats.

Thus, egg yolks are very high in fats, but low in proteins; while egg whites are very high in proteins, but low in fats. However, egg yolks do contain some proteins, and egg whites do contain small quantities of fats.

Due to their different compositions and uses, it is often desirable to separate egg yolks and egg whites from one another. Various systems and methods have been developed for separation of eggs into yolks and whites. Separation of yolk and white from whole eggs can be done at high speeds under automated conditions, and can very effectively separate the yolks and eggs, with relatively little mixing of the yolk and eggs.

Despite the uses of existing technology to separate yolks from whites, a need exists for further separation of egg components, including components in both the egg yolk and the egg white. This is true because the mere physical separation of the egg yolk from the egg white is not always sufficient to maximize use of the yolks and whites. For example, with regard to the yolk, it can desirable to also remove the yolk proteins from the yolk fats for at least two reasons: First, traditional uses of the yolk as an emulsifier improve upon reduction of the protein content. Second, the removal of the protein provides an isolated protein material that has further uses for applications where high-protein materials are desired and where specific yolk proteins are desired in isolated form. Similarly, with regard to the egg white, removal of non-protein materials creates a higher quality isolated protein. Also, separation of the proteins into different sizes and types can have significant benefits for production of specialized products.

In addition to the benefits associated with separating proteins and fats from nearly pure egg yolks and pure egg whites, a need also exists for separation of proteins and fats from mixtures that contain both egg yolks and egg whites. Such mixtures are created, for example, as a result of incidental breakage of yolks during the separation of the yolk from the white during the cracking process. Similarly, some egg white can remain with the egg yolk during cracking. These mixtures result in increased levels of proteins in the separated egg yolk, and increased levels of fats in the separated egg whites. The ability to separate the primary constituents (proteins and fats) within the mixtures can have meaningful advantages in terms of nutritional value and performance for specific applications (such as to create mayonnaise).

Yet another scenario for separation of fats and proteins in eggs arises due to production of eggs at hatcheries (or other facilities) where the eggs are not primarily raised for human consumption. For example, sterile eggs and non-incubated eggs from hatcheries are not produced or used for human consumption. Although these hatchery-derived eggs are typically not provided for regular human consumption, they are still of value as a source of fats and proteins. Currently the hatchery-derived eggs are not processed so as to be separated into yolk and white components, because they are produced in facilities that are not served by a high speed cracker and separator. Instead, the hatchery-derived eggs are often broken and the contents run through a separator to remove the egg shells, a process that mixes the egg yolks and proteins. This mixed egg yolk and white, which is considered inedible for human consumption, is typically used as a combined additive for uses such as animal feed. However, a need exists for a means for effectively separating the fats and proteins from these mixtures of inedible eggs so as to gain the maximum benefit of the proteins and fats so that they may be used in the most desirable manner. This is best achieved by separating them from one another.

As noted above, the most prevalent means of separating egg components is limited to the separation of whole yolks and whites from one another. This separation is commonly performed at high speeds and efficiencies using automatic equipment. However, alternative efforts for further separation of egg components into more isolated components have been attempted. Unfortunately, these methods have proven problematic for various reasons, including because the processes are inefficient, impractical, or have other deficiencies.

An example of such efforts is found in U.S. patent application Ser. No. 11/971,802 ("the '802 application"), assigned to Biova, Inc., and which is directed to a method of separating lipids from an egg mixture by using a cross-linking reagent. The cross-linking reagent is added to an egg mixture containing lipids and solubilized proteins, causing the lipids to crosslink so they can be separated from the proteins. Suitable crosslinking reagents include cyclobetadextran, silicon dioxide, colloidal silica material, fumed silica materials, and synthetic calcium silicate hydrates. The method of the '802 application may can include adjusting the pH level of the egg mixture to a pH at which the cross-linking reagent is functional so that cross-linking of the lipids occurs. The proteins are subsequently separated from the cross-linked lipids to provide a separated protein. The separated proteins may be obtained by subjecting the egg mixture to one or membranes or filters of various sizes to separate or further isolate proteins or populations of proteins of interest.

Although it may be possible to separate proteins and fats derived from eggs using the teachings of the '802 application, significant drawbacks are associated with the methods and materials it discloses. First, the inclusion of the cross-linking reagent is problematic if the egg components will eventually be consumed by humans, in that there is often opposition on the part of the public and regulatory agencies to consume materials that have been subject to adulteration by organic reagents, such as cyclobetadextran, or by inorganic materials such as colloidal or fumed silica materials. The aversion to the use of these cross-linking reagents exists, in part, because of the potential for undesirable modification or contamination of the crosslinked ingredients. Although naturally occurring silica is widespread in nature, its use in food processing is unusual, and risks opposition by consumers even if little or none of the crosslinking agent remains in the separated components.

Second, the use of the crosslinking reagent necessarily adds expense to the processing of the egg mixture, both because of the cost of the crosslinking reagent itself, as well as the costs associated with the additional steps of crosslinking the fats and subsequent removal of the crosslinking agent (such as silica) from the fats after separation of the fats and proteins, assuming the fats are intended for further use. Thus, not only does the use of a reagent result in potentially problematic alteration and/or contamination of the egg material with crosslinker, especially the egg yolk (since it is the fats that are crosslinked, and fats are primarily found in the yolk), but the use of the reagent adds expense and complexity to the egg processing methods: A step must be made to add the reagent to the egg mixture, one to induce crosslinking of the fats, as well as steps to reverse the crosslinking, when possible, after separation of the crosslinked egg fats and egg proteins. These steps all take time, equipment, and effort.

Yet another problem with the methods taught in the '802 application is that the use of the reagents creates an issue with regard to waste silica (or other crosslinking agent), which must be removed from the fats for most uses of the fats, and which can result in creation of an undesirable waste stream that must be disposed of, even if it is not hazardous. Today there is an increased emphasis on processes that use limited resources and which produce little or no waste product, and the '802 application does not fully satisfy this objective.

Therefore, a need exists for methods and equipment for separating egg components into proteins and fats (or other substituents, such as amino acids). Such methods and equipment should include the ability to separate the components of exclusively egg yolk materials, exclusively egg white materials, and mixtures of various levels of egg yolk and egg white. Preferably such methods and equipment can be efficient, cost effective, produced without undesirable alteration of the egg components (such as alteration with cross linkers), and do not create excessive undesirable waste streams.

SUMMARY OF THE INVENTION

The invention described herein provides a method for separating fats and proteins from an egg mixture that includes both egg yolk and egg whites, as well as separation of components from pure egg white and separation of components from pure egg yolks. The methods and systems of the present invention allow the ready separation of the ingredients of an egg, regardless of whether the separation is occurring on just a portion of an egg (such as the yolk or the white), or a mixture of egg yolks and egg whites.

Significantly, the present invention does not require alteration of either the fats or the proteins with a reagent or by manipulation of pH. Thus, the present invention allows the integrity of the egg ingredients to be maintained so as to avoid undesirable alteration, such as incorporation of a crosslinker. As such, the present invention also avoids extra production steps and does not produce a new waste stream associated with use of a crosslinking reagent.

The method comprises obtaining an egg mixture containing egg-derived lipids and egg-derived proteins; and microfiltration of the egg mixture to obtain an isolated protein composition. An example implementation of the present invention comprises obtaining an egg mixture containing egg yolk lipids, egg yolk proteins, and egg albumen; and microfiltration of the egg mixture to obtain an isolated protein composition containing yolk-derived proteins and albumen-derived proteins.

As will be more specifically described below, the microfiltration occurs under conditions whereby the selection of the filter materials, as well as the filter configuration, provide improved separation of egg components while avoiding fouling of the filter materials.

In one embodiment, the filter incorporates hollow fiber membranes constructed from a hydrophilic material. In example embodiments, the hollow fiber membranes are constructed from polysulfone (PS) or polyether sulfone (PES). In an alternative embodiment, hollow fiber ceramic material is used. Multiple membrane modules can be used, typically in series. Generally at least two membrane modules are used, often three of four membrane modules in series. Some modules can also be arranged in parallel, and it is possible to have configurations with both serial and parallel membranes. Notably, in some implementations the modules are arranged so that some membrane modules are taken offline for cleaning while other membrane modules are being actively used. Thus, if four membrane modules are desirable, the system may have five modules, with any one module being down for cleaning at any time. Rotation of the modules that are being cleaned allows for ongoing production as well as maintaining production levels by allowing membranes to be cleaned.

In an alternative embodiment, a spiral wound membrane module is used. The membranes forming the spiral wound membrane module may be, for example, formed of polyvinylidene fluoride (PVDF). Preferably the spiral wound membrane modules include spacers between membrane layers.

Suitable spacing is generally greater the 30 mils, more generally greater than 45 mils, and in some implementations greater than 60 mils. Again, various combinations of serial and parallel membrane modules can be used. Also, it will be understood that the modules do not all need to be the same: Some can be PS, some can be PES, and/or some can be PVDF (or another material).

In a specific implementation, a method for separating proteins and lipids from an egg mixture is described, and the method comprises obtaining an egg mixture containing egg yolk lipids and egg yolk proteins; and microfiltration of the egg mixture to separate the egg yolk lipids from the egg yolk proteins. The method for separating proteins from an egg mixture can include the steps of obtaining an egg mixture comprising egg yolk and egg albumen; maintaining the pH of the egg yolk and egg albumen within the natural range of egg pH; and microfiltration of the egg mixture to obtain a isolated protein composition containing yolk-derived proteins and albumen-derived proteins. In this manner superior protein recovery is obtained over prior art methods, because both yolk-derived proteins and albumen-derived proteins are isolated and obtained. Simultaneously, the remaining egg yolk is improved by removal of the proteins, which do not generally have primary functional benefits for the applications where yolk fats are desired (such as emulsifiers).

In certain implementations the method comprises obtaining an egg mixture comprising egg yolk and egg albumen and maintaining the lipids in a substantially un-crosslinked form. The mixture is microfiltered to obtain an isolated protein composition containing yolk-derived proteins and albumen-derived proteins. The egg mixture initially comprises between about 40% and 70% protein by weight and between about 15% and 45% fat by weight. Variations in the protein and fat compositions occur depending upon the source of the egg materials: Sources that are high in egg whites, such as from spinning of egg shells, will be high in protein; while those that have more yolk based material, such as whole eggs from hatcheries, will have relatively higher fat levels and relatively lower protein levels.

The invention is further directed to an egg powder obtained from egg yolks and/or egg albumen. In an example embodiment the egg powder comprises at least about 60% by dry weight protein; and less than about 2% by dry weight fat; wherein at least a portion of the protein is derived by filtration of a mixture of egg yolk lipids and egg yolk proteins.

A high gel strength egg powder can further be created, the egg powder comprising in an example implementation at least about 60% by weight protein; no more than about 1% by weight fat; and a gel strength of at least 400, wherein at least a portion of the protein is derived by filtration of a mixture of egg yolk lipids and egg yolk proteins. In some implementations higher levels of protein are present, including at least 70% by weight protein, at least 75% by weight protein, at least 80% by weight protein, at least 85% by weight protein, or at least 90% by weight protein. Also, it is possible to have very low weight percents of fat in some implementations, including less than 0.5% by weight fat; less than 1.0% by weight fat; less than 2.5% by weight fat; less than 5.0% by weight fat in some implementations.

The methods and apparatus of the present invention can be used for separating components of both edible and inedible eggs, where inedible eggs include (for example) hatchery eggs that are not fertilized or not incubated.

As discussed above, the method of the invention includes a step of microfiltration of the egg mixture, wherein the microfiltration step includes pumping the egg mixture across a filter, optionally a hollow fiber filter. The hollow fiber filter will generally have a pore size of less than 0.20 microns, and more generally less than 0.10 microns. The pore size of the filter is typically greater than 0.02 microns. Suitable pore sizes for the filter include approximately 0.05 microns, as well as 0.04 to 0.08 microns.

The egg mixture is generally processed in the filter at low pressures. In one implementation the egg mixture is processed at a pressure of less than about 30 PSI. Optionally the pressure can be less than 20 PSI in some implementations. Higher PSI can be used, but can result in premature fouling of the filter membrane and also result in rupturing the membrane in some situations. Thus, pressures of less than 40 PSI, less than 50 PSI, and less than 100 PSI are useful in some implementations, but generally lower pressures are desired. A pressure range of 10 to 30 PSI can be particularly useful.

In some example implementations the egg mixture is processed at a pressure of approximately 10 psi baseline pressure plus 10 to 15 psi for each membrane module in series in the system (often about 13 psi for each membrane). For example, a system with two membrane modules might have an inlet pressure of 36 psi and an outlet pressure of 10 psi.

In other example implementations the egg mixture is processed at a pressure of approximately 2 psi baseline pressure plus 6 psi for each membrane module in series in the system. For example, a system with two membrane modules might have an inlet pressure of 14 psi and an outlet pressure of 2 psi. In yet another example implementations the egg mixture is processed at a pressure of approximately 1 to 4 psi baseline pressure plus 5 to 10 psi for each membrane module in series in the system. For example, a system with two membrane modules might have an inlet pressure of 11 to 24 psi and an outlet pressure of 1 to 4 psi. In alternative example implementations the egg mixture is processed at a pressure of less than 5 psi baseline pressure plus less than 10 psi for each membrane module in series in the system. In other example implementations the egg mixture is processed at a pressure of less than 5 psi baseline pressure plus less than 7 psi for each membrane module in series in the system.

The flux rate is typically in a range of about 40 to 80 milliliters per minute per square foot of membrane, with the permeate being (for example) from 3 to 5 percent solids when the incoming material is about 10 percent solids.

In some implementations water is added to the egg mixture before separation. Such added water, also referred to as diafiltration water, can meaningfully increase the recovery of proteins. In some implementations the diafiltration water is added at a rate of between 10 and 250 percent of the original liquid volume. In some implementations the diafiltration water is added at a rate of between 10 and 150 percent of the original liquid volume, while in yet other implementations the diafiltration water is added at a rate of 10 to 100 percent of the original liquid volume. Optionally, the diafiltration water is added at less than 250 percent, less than 200 percent, less than 150 percent, less than 100 percent, less than 50 percent, less than 25 percent, or less than 10 percent of the original liquid volume. Generally higher diafiltration water levels are desirable when fat levels are high, or protein levels are low, because the additional water can help remove proteins. Thus, in egg mixtures that have a high fat content, such as egg yolk, higher levels of diafiltration water can be desirable. For example diafiltration water can be added at 250 to 500 percent of the original egg mixture, or from 250 to 500 percent of the original egg mixture, or from 500 to 1000 percent of the original egg mixture in some implementations. These high diafiltration addition rates are particularly useful for high fat egg mixtures (such as primarily egg yolks)

The invention also provides a high gel strength egg powder, wherein the egg powder includes less than neg/25 g *salmonella*; at least about 65% by dry weight protein; and no more than about 1% by dry weight fat. The egg powders can be produced from edible or inedible eggs. Higher protein levels can be obtained, including levels of 70 to 85% by dry weight protein. The egg powder can have a high gel strength that is greater than 300 grams per square centimeter, more commonly greater than 400 grams per square centimeter, and desirably 500 or more grams per square centimeter.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE DRAWINGS

The invention will now be understood by review of the following drawings.

Figure 1:
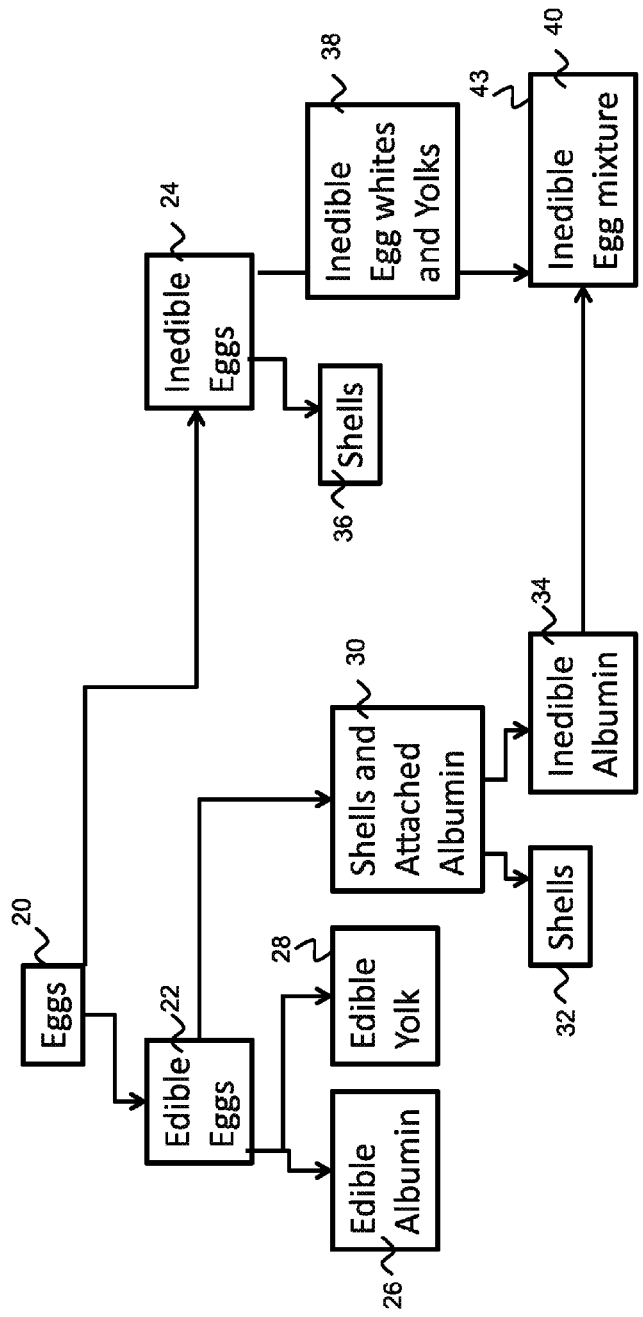
FIG. 1 is a flow chart of an egg separation process described herein, constructed and arranged in accordance with an implementation of the invention.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION

Whole egg components generally include an eggshell, two eggshell membranes, and an egg white and an egg yolk. The egg white makes up about two-thirds of the liquid weight of the egg, with the egg yolk making up approximately the remaining one-third. Both the egg white and the egg yolk contain nutritionally valuable components such as proteins and fats (also called lipids). The different egg components impart various "functional properties" to the egg. The term "functional properties" refers to the properties of eggs and egg components, including but not limited to, coagulation, foaming, emulsifying, and nutritional contribution.

The main components of the egg white (the albumen) include water (approx. 90% by weight) and solids (approx. 10% by weight) such as proteins, trace minerals, fatty material (less than 0.4%), vitamins and glucose, with protein making up the majority of the solids. In fact, the egg white contains approximately 40 different proteins. The predominant proteins in albumen include: Ovalbumen, Ovotransferrin, Ovomucoid, Globulins, Lysozyme, Ovomucin, and Avidin.

The egg yolk includes protein, fat, water, vitamins, minerals and other trace elements. As used herein, the term "fat" refers to lipids. The most prevalent lipids in egg yolk include: unsaturated fatty acids (Oleic acid, Linoleic acid, Palmitoleic acid, and Linolenic acid) and saturated fatty acids (Palmitic acid, Stearic acid, and Myristic acid). The yolk is also a source of lecithin, a common emulsifier, and proteins, including but not limited to immunoglobulins such as IgY and/or ovatransferin.

Each of the various egg components has utility in a variety of industries. However, even though it is recognized that eggs contain numerous valuable components, problems remain with respect to recovery and/or separation of such components in efficient and cost-effective ways.

Commercially produced chicken eggs for human consumption often originate in egg laying operations where non-fertile eggs are produced and collected. After being collected, transferred to a processing facility and washed, the eggs are graded as either edible or inedible. Eggs that have met an edible grade category are then graded AA, A or B. Eggs that are labeled inedible are not suitable for human consumption based on the USDA or other government regulations. About 98% to 99% of eggs meet a grade category of AA, A or B. The remaining 1% or 2% are considered inedible (i.e., not suitable for human consumption). The primary reason an egg is considered inedible is that the egg is malformed or contains discrete blood spots. Otherwise, the product is generally safe for human consumption.

After the eggs are initially graded as edible or inedible, the eggshell of the edible eggs can be broken using an egg breaking machine. The whole egg (egg yolk and egg white) mixture is then strained to separate the egg yolk from the egg white (the yolk is retained while the white passes through the strainer). Once the yolk is separated from the egg white, additional processing of the egg white and/or the yolk often occurs.

The broken shells from the edible eggs are typically spun via a centrifuge system to extract the egg white that remains adhered to the broken eggshells. The extracted egg white is also considered inedible (e.g., not usable for human consumption). The broken eggshells can be dried and ground up to be used as an ingredient in animal feeds and other products, among other uses.

Another source of eggs comes from hatcheries intended to produce chicks. Some of the eggs from hatcheries do not hatch, often because they are infertile, are not incubated, or are not incubated to full development. These eggs often are handled as inedible eggs—either by choice (such as in eggs that are not incubated) or due to regulatory requirements (such as, for example, eggs that are not incubated to full development). Hatchery eggs are typically processed without separation of the yolk and white in a process whereby they are cracked and processed as a combination of yolk and whites.

Thus, three major sources of inedible egg products exist: eggs that were produced to be edible but are graded as inedible, egg components that are collected from egg shells, and eggs that originated from hatcheries. Other sources also exist, such as eggs that are returned from food processors (such as due to passing freshness dates), eggs that missed the pan during cracking operations, or otherwise deemed to be technical (or inedible) eggs by the USDA or other regulators. These inedible eggs and mixtures of egg components are frequently used in animal food products. Examples of animal food products include but are not limited to "wet" pet foods such as canned dog and cat food, dry pet foods, and weanling pig feed. Although these uses of inedible egg mixtures are desirable, the present products are relatively low value because they are not modified or processed in a manner that optimizes uses and performance. Therefore, a need exists for improved processing of inedible egg mixtures. This improved processing also has the potential for improved processing of edible egg mixtures.

Significantly, the present invention does not require alteration of either the fats or the proteins with a reagent or manipulation of pH. Thus, the present invention allows the integrity of the egg ingredients to be maintained so as to avoid undesirable alteration, such as incorporation of a crosslinker. As such the present invention also avoids extra production steps and does not produce a new waste stream associated with use of a crosslinking reagent The method comprises obtaining an egg mixture comprising egg-derived lipids and egg-derived proteins; and microfiltration of the egg mixture to obtain an isolated protein composition. An example implementation of the present invention comprises obtaining an egg mixture comprising egg yolk lipids, egg yolk proteins, and egg albumen; and microfiltration of the egg mixture comprising egg yolk lipids, egg yolk proteins, and egg albumen to obtain a isolated protein composition containing yolk-derived proteins and albumen-derived proteins.

As will be more specifically described below, the microfiltration occurs under conditions whereby the selection of the filter materials, as well as the filter configuration, provide improved separation of egg components while avoiding fouling of the filter materials. In one embodiment, the filter incorporates hollow fiber membranes constructed from a hydrophilic material. In example embodiments, the hollow fiber membrane is constructed from polysulfone (PS) or polyether sulfone (PES). In an alternative embodiment, a spiral wound membrane module is used. The membranes forming the spiral wound membrane module may, for example, be formed of polyvinylidene fluoride (PVDF). Preferably the spiral wound membrane modules include spacers between membrane layers. Suitable spacing is generally greater the 30 mils, more generally greater than 45 mils, and in some implementations greater than 60 mils.

Multiple membrane modules can be used, typically in series. Generally at least two membrane modules are used, often three of four membrane modules in series. Some modules can also be arranged in parallel, and it is possible to have configurations with both serial and parallel membranes. Notably, in some implementations the modules are arranged so that some membrane modules are taken offline for cleaning while other membrane modules are being actively used. Thus, if four membrane modules are desirable, the system may have five modules, with any one module being down for cleaning at any time. Rotation of the modules that are being cleaned allows for ongoing production as well as maintaining production levels by allowing membranes to be cleaned.

The membrane module, however configured, should primarily allow proteins to pass, while avoiding passing of larger lipids. Specifically, the membrane should be selected so as to substantially restrict the passage of lipids from the egg mixture, while allowing the passage of proteins from the egg mixture. Generally, the membrane should have pore sizes of less than 0.5 microns, more typically less than 0.4 microns, and usually less than 0.3 microns. It will be understood that in some implementations the pore size will be less 0.2 microns. Optionally, the pore size is less than 0.1 microns. Pore size ranges of 0.1 to 0.2 microns are desirable in some implementations, as are pore sizes of 0.05 to 0.3 microns in some implementations.

In some implementations, the PVDF is selected to have a nominal cutoff of 800,000 dalton, in other implementations the PVDF is selected to have a nominal cutoff of greater than 700,000 dalton, greater than 600,000 dalton, or greater than 500,000 dalton. In other implementations the PVDF is selected so as to have a nominal cutoff of greater than 800,000 dalton, greater than 900,000 dalton, or greater than 1,000,000 dalton. The PVDF can be selected so as to have a nominal cutoff of less than 900,000 dalton, less than 800,000 dalton, less than 700,000 dalton, less than 600,000 dalton, and less than 500,000 dalton. Typically the PVDF will have a nominal cutoff of from 600,000 to 1,000,000 dalton, or from 700,000 to 900,000 dalton.

Suitable membranes include ultra filtration membranes produced by Snyder Filtration, located in Vacaville, Calif., including 0.2 and 0.1 micron PVDF filters.

The invention described herein provides a method for processing an egg mixture that contains egg yolk and egg albumen, or just egg yolk or egg albumen, to separate proteins and fats. As used herein the term protein refers to organic compounds made of amino acids (polypeptides) and includes, but is not limited to, proteins such as immunoglobulins, for example, IgY. As used herein, the term "fats" can be used interchangeably with "lipids" and refers to water-insoluble components such as fatty acids, steroids, such as cholesterol, glycolipids, lipoproteins and phospholipids.

In one embodiment, the invention relates to processing of an edible or inedible egg mixture. In a more particular embodiment, the invention provides a method of processing an edible or inedible egg mixture to obtain an egg protein powder (which will be edible or inedible based upon whether the source eggs were edible or inedible). In a specific embodiment, the egg mixture comprises between about 40%-70% protein by weight and between about 15%-45% fat. Typically this mixture will have the fat and protein intermixed to some degree, but the mixture is not actually homogenized. Indeed, it is generally desirable to maintain some separation of the components of the egg yolk and egg whites, and therefore lower levels of mixing can be desirable. Although homogenized egg products are often less desirable for use with the present invention, it is possible to use egg compositions that include some homogenized egg materials. For example, homogenized eggs that were originally edible, but have expired due to prolonged shelf life, can be considered to be inedible and processed using the methods and apparatus of the invention.

The method includes a step of microfiltration of the egg mixture, wherein the microfiltration step includes pumping the egg mixture across a filter, optionally a hollow fiber filter. The hollow fiber filter will generally have a pore size of less than 0.20 microns, and more generally less than 0.10 microns. The pore size of the filter is typically greater than 0.02 microns. Suitable pore sizes for the filter include approximately 0.05 microns, as well as 0.04 to 0.08 microns.

The egg mixture is generally processed in the filter 60 at low pressures. In one implementation the egg mixture is processed at a pressure of less than about 30 PSI. Optionally the pressure can be less than 20 PSI in some implementations. Higher pressures can be used, but can result in premature fouling of the filter membrane. Thus, pressures of less than 40 PSI, less than 50 PSI, and less than 100 PSI are useful in some implementations, but generally lower pressures are desired. In some example implementations the egg mixture is processed at a pressure of approximately 10 psi baseline pressure plus 10 to 15 psi for each membrane module in series in the system (often about 13 psi for each membrane). For example, a system with two membrane modules might have an inlet pressure of 36 psi and an outlet pressure of 10 psi. In other example implementations the egg mixture is processed at a pressure of approximately 2 psi baseline pressure plus 6 psi for each membrane module in series in the system. For example, a system with two membrane modules might have an inlet pressure of 14 psi and an outlet pressure of 2 psi. In yet another example implementations the egg mixture is processed at a pressure of approximately 1 to 4 psi baseline pressure plus 5 to 10 psi for each membrane module in series in the system. For example, a system with two membrane modules might have an inlet pressure of 11 to 24 psi and an outlet pressure of 1 to 4 psi. In an alternative example implementations the egg mixture is processed at a pressure of less than 5 psi baseline pressure plus less than 10 psi for each membrane module in series in the system. Another example implementations the egg mixture is processed at a pressure of less than 5 psi baseline pressure plus less than 7 psi for each membrane module in series in the system.

As noted above, in some implementations the egg mixture is processed using a PVDF spiral wound membrane filter. In such implementations, multiple modules may be used. In some example implementations the egg mixture is processed at a pressure of approximately 10 psi baseline pressure plus 10 to 15 psi for each membrane module in series in the system (often about 13 psi for each membrane). For example, a system with two membrane modules might have an inlet pressure of 36 psi and an outlet pressure of 10 psi.

When using a hollow fiber membrane, the flux rate is desirably in a range of about 40 to 80 milliliters per minute per square foot, with the permeate being from 3 to 5 percent solids when the incoming material is about 10 percent solids. In one embodiment, the filter incorporates hollow fiber membranes constructed from a hydrophilic material. The hollow fiber membrane can be constructed from, for example, polysulfone (PS) or polyether sulfone (PES). In an alternative embodiment, a spiral wound membrane module is used, and has a flux rate of greater than 4 liters per hour per square media of membrane. Preferably even higher fluxes are achieved, such as greater than 6 liters per hour per square meter of membrane. The membranes forming the spiral wound membrane module may be, for example, be formed of polyvinylidene fluoride (PVDF). Preferably the spiral wound membrane modules include spacers between membrane layers. Suitable spacing is generally greater the 30 mils, more generally greater than 45 mils, and in some implementations greater than 60 mils.

Spiral wound modules can be susceptible to fouling, and therefore it is often desirable to design and operate a system utilizing clean in place (CIP) processes, so that the membranes can be cleaned without shutting down the entire system or stopping the separation process. Such cleaning often occurs more than once per 24 hour period, in some implementations less than every 16 hours, and in certain implementations approximately every 8 hours.

The invention also provides a non-food grade egg powder obtained from inedible egg and a high gel strength inedible egg powder, wherein the egg powder includes less than neg/ 25 g *salmonella*; at least about 65% by weight protein; and no more than about 1% by weight fat. The high gel strength inedible egg powder can have a high gel strength that is greater than 300 grams per square centimeter, more commonly greater than 400 grams per square centimeter, and desirably 500 or more grams per square centimeter.

Referring now to the drawings, FIG. 1 depicts an example flow diagram of an egg processing method. Eggs 20 are collected from egg barns (not shown). The eggs 20 are separated into edible 22 and inedible 24 eggs. The edible eggs 22 are then broken and the edible albumen 26 and the edible yolk 28 are transported for further processing for human consumption. Dried edible albumen 26 contains no yolk protein and approximately 0.4% by weight fat. The edible yolk 28 contains about 30% by weight protein and approximately 60% by weight fat.

The eggshells 30 with residual albumen adhered thereto are sent down a separate processing line where they are then centrifuged, separating the shells 32 from the residual albumen, which is now classified as inedible albumen 34.

The inedible eggs 24 are also broken and the shells 36 processed. The white and yolk 38 from the inedible eggs 24 are mixed with the inedible albumen 34 extracted from the shells to form an inedible egg mixture 40. The inedible egg mixture 40 is an uncooked and unprocessed liquid mixture containing both egg yolk (including yolk fat and proteins), along with the egg white (and associated proteins). The inedible egg mixture generally includes between about 40%-70% by dry weight protein and between about 40%-15% by dry weight fat.

Typically, the inedible egg mixture 40 is maintained at a temperature of less than approximately 50° F. and a pH above approximately 5.75 to 7.00, or optionally from about 4.0 to 8.0. Frequently caramel coloring is added into the egg mixture 40 to identify the mixture as inedible. As such, the vessel 43 in which the inedible egg mixture 40 is maintained may include an agitator or paddle to mix the liquid egg mixture.

Figure 2:
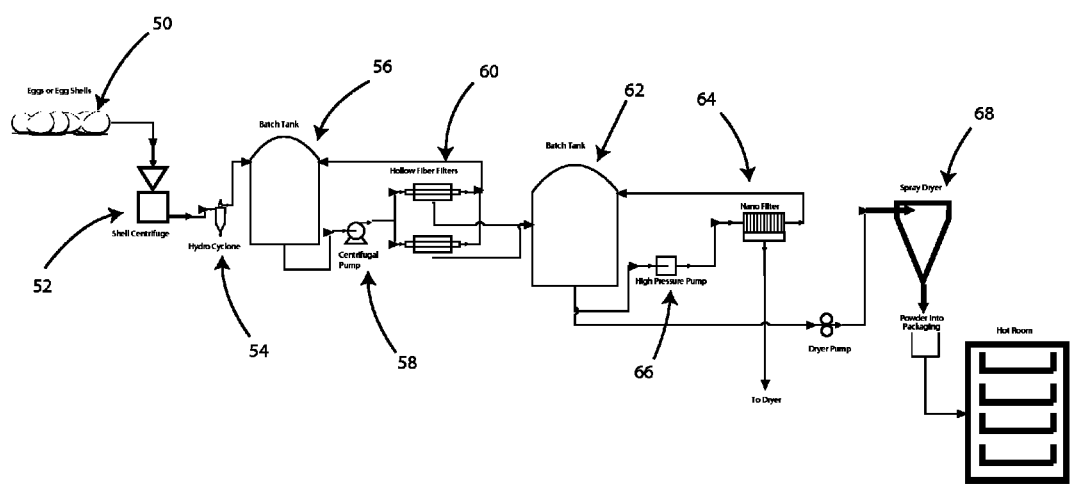
FIG. 2 is a schematic of an egg separation process described herein for an egg breaking operation, such as with eggs from a hatchery, constructed and arranged in accordance with an implementation of the invention.

FIG. 2 provides a schematic of a process for separating proteins and fats from an egg mixture according to the invention from an example breaking operation (such as from hatchery eggs that were not incubated). According to the process shown in FIG. 2, the eggs 50 are first broken and the liquid egg (i.e., egg yolk and egg whites) are removed. As noted above, the eggs are typically inedible eggs, but optionally can be edible eggs. The shells with residual egg adhered thereto are transported to a shell centrifuge 52 where centrifugal force is used to separate the residual liquid egg from the shell particulate matter. The processed shell particulate matter can then be collected, processed and sold, for example, for use as a calcium supplement. The extracted residual egg liquid can be drained into a collecting vat and sold, for example, as animal food, stored, or subject to further processing.

In one embodiment, the liquid egg is removed from the shell centrifuge and run through a hydrocylcone 54 to remove suspended calcium. The liquid egg material is collected in a tank 56. A pump, for example, a centrifugal pump 58 can be used to pump the liquid egg material through a microfiltration membrane 60. Multiple membranes can be provided, The method further includes a step of microfiltration of the egg mixture, wherein the microfiltration step includes pumping the egg mixture across a filter, optionally a hollow fiber filter. The combination of pressure, flux (i.e., the tangential flow of the liquid across the surface of the membrane) and membrane pore size can significantly impact filter performance. The hollow fiber filter will generally have a pore size of less than 0.20 microns, and more generally less than 0.10 microns. The pore size of the filter is typically greater than 0.02 microns. Suitable pore sizes for the filter include approximately 0.05 microns, as well as 0.04 to 0.08 microns.

The egg mixture is generally processed at low pressures. In one implementation the egg mixture is processed at a pressure of less than about 30 PSI. Optionally the pressure can be less than 20 PSI in some implementations. Higher PSI can be used, but can result in premature fouling of the filter membrane. Thus, pressures of less than 40 PSI, less than 50 PSI, and less than 100 PSI are useful in some implementations. The flux rate is desirably in a range of about 40 to 80 milliliters per minute per square foot of filter membrane, with the permeate being from 3 to 5 percent solids when the incoming material is about 10 percent solids.

As noted above, in some implementations the egg mixture is processed using a PVDF spiral wound membrane filter. In such implementations, multiple filter modules may be used (although single membrane modules are used in some implementations). In some example implementations the egg mixture is processed at a pressure of approximately 10 psi baseline pressure plus 10 to 15 psi for each membrane module in series in the system (often about 13 psi for each membrane). For example, a system with two membrane modules might have an inlet pressure of 36 psi and an outlet pressure of 10 psi.

The egg mixture may be processed at various temperatures, with 65 to 70 degrees Fahrenheit being desirable, as well as 60 to 75 degrees Fahrenheit. In the alternative, other temperature ranges may be used. In some implementations the temperature is very close to 70 degrees Fahrenheit, such as 68 to 72 degrees Fahrenheit. Generally the temperature is kept at or below 80 degrees Fahrenheit, and more commonly below 70 degrees Fahrenheit.

It is believed that the relatively low pressure reduce the amount of fat that is forced into the pores of the filter membrane. When the low pressure is combined with a relatively high tangential velocity of fluid across the surface of the membrane, the fat (retentate) is forced to flow past the membrane while allowing the protein (the permeate) to pass through the membrane pores. As such, the amount of fat deposited on the filter is significantly reduced and performance is enhanced. To further reduce the amount of fat deposited on and fouling the membrane, the hollow fiber membrane can be constructed using a hydrophilic material such as polysulfone (PS) or polyester sulfone (PES). Polyvinylidine fluoride (PVDF) is another suitable material for use in the processes of the present invention, and are typically formed into spiral wound membrane modules.

The liquid permeate that contains the protein can be collected in a second batch tank 62 and the retentate, which includes the fat, residual proteins and other solids such as bacteria, can optionally be returned to the first batch tank. If desired, water can be added to the first batch tank 56 and the retentate liquid can be again pumped through the hollow fiber filter membrane 60 to increase yield.

In some implementations water is added prior to separation at the hollow fiber filter membrane 60. Such added water, also referred to as diafiltration water, can meaningfully increase the recovery of proteins. In some implementations the diafiltration water is added at a rate of between 10 and 250 percent of the original liquid volume. In some implementations the diafiltration water is added at a rate of between 10 and 150 percent of the original liquid volume, while in yet other implementations the diafiltration water is added at a rate of 10 to 100 percent of the original liquid volume. Optionally, the diafiltration water is added at less than 250 percent, less than 200 percent, less than 150 percent, less than 100 percent, less than 50 percent, less than 25 percent, or less than 10 percent of the original liquid volume. In certain embodiments water is added at approximately 10 to 40 percent, optionally 20 to 30 percent, of the original egg mixture volume.

In egg mixtures that have a high fat content, such as egg yolk, higher levels of diafiltration water can be desirable. For example diafiltration water can be added at 250 to 500 percent of the original egg mixture, or from 250 to 500 percent of the original egg mixture, or from 500 to 1000 percent of the original egg mixture in some implementations. These high diafiltration addition rates are particularly useful for high fat egg mixtures (such as primarily egg yolks)

This process can be repeated until about 95% of the protein has been recovered (i.e., has permeated the filter) in some implementations, and up to about 85 percent in other implementations. This recovery rate, also referred to as yield, is generally greater than 60 percent. If desired, phospholipids such as phosphotidyl choline can also be separately extracted from the fat containing retentate.

The liquid protein solution (permeate) from the second batch tank 62 can be further isolated, for example by pumping the liquid permeate through a nanofilter 64 using a high pressure pump 66. In one embodiment, the protein solution is isolated to a solution containing approximately 20%-35% by weight solids. A isolated protein solution is desirable because drying time, and hence cost, can be reduced. Additionally, the nanofiltration step can also reduce the amount of ash present in the final isolated protein solution. In one embodiment, a spiral wound nanofilter is used to concentrate the protein solution. If desired, functional proteins such as lysozyme or immunoglobulins, such as IgY, can be separated from the liquid protein solution prior to nanofiltration. When nanofiltration is completed, the pH of the isolated protein solution can be adjusted and yeast added to convert sugars present in the solution to carbon dioxide. Next, the isolated protein solution is dried using a spray dryer 68.

In one embodiment, the process of the invention is used to provide an egg protein powder containing proteins that are derived from the egg yolk and the egg white. In another embodiment, the egg protein powder can be dissolved in water and cooked to form a gel that binds the water in which the powder was dissolved. For example, the powder can be packaged or placed in a hot humid room with a temperature from 165° F. to 175° F. and humidity of 30 to 40 percent for multiple days (generally 10 to 20 days) to denature the protein and increase gel strength.

Protein powders with the following gel strength can be obtained by the process described herein, and are compared to standard whole egg powder (48% protein by weight) which has a 150 gel strength:

(a) 65% protein by dry weight egg powder (higher egg white content—200 gel strength—comparable product to US wheat gluten)

(b) 80% by dry weight standard egg white powder—not hot room treated—250 gel strength (c) standard edible egg white powder—hot roomed for gel—400 gel strength (d) high gel strength inedible egg powder—hot roomed for gel—500/550 gel strength.

The invention is further directed to an egg powder obtained from egg yolks and/or egg albumen. In an example embodiment the egg powder comprises at least about 60% by dry weight protein; and less than about 2% by dry weight fat; wherein at least a portion of the protein is derived by filtration of a mixture of egg yolk lipids and egg yolk proteins.

A high gel strength egg powder can be created wherein the egg powder comprising at least about 60% by weight protein; no more than about 1% by weight fat; and a gel strength of at least 400, wherein at least a portion of the protein is derived by filtration of a mixture of egg yolk lipids and egg yolk proteins. In some implementations higher levels of protein are present, including at least 70% by weight protein, at least 75% by weight protein, at least 80% by weight protein, at least 85% by weight protein, or at least 90% by weight protein. Also, it is possible to have very low weight percents of fat in some implementations, including less than 0.5% by weight fat in some implementations.

An example method of measuring gel strength is as follows: Weigh up 25 g of whites into a whirl-pack bag. Add 175 ml of distilled water to the bag, and place it in a stomacher in continuous mode for 5 minutes, followed by removal of the bag from stomacher and letting it sit for 15-20 minutes. Next, pipet approximately 125 ml of whites into a casing, and let sit another 3-5 minutes. After 3-5 minutes tap the sides of casing to remove air bubbles that have collected on sides. Clasp the casing at top end just below the top foam and twist tightly, and secure with a twist tie at base of twist and then fold over and secure with rest of twist tie. Next, rinse off the casing with deionized water and place in an 80° C. water bath for 40 minutes. After 40 minutes remove the casing from the water bath, and cool down with cold running tap water for 5-10 minutes. Lace the casing in a refrigerator overnight. The next morning take the casing out of refrigerator for 1 hour.

Using a Rheo meter, use an 8 mm diameter ball as a plunger and set the range switch at 200/2N for low get and at 2 k/20N for high gel testing. The table speed should be set at 6 cm/min. Cut off end of casing and peel off, cutting the sample into 3-4 pieces that are 30 mm long. Place a sample piece in the center of the table and press the table button and lift up to just under plunger. Then press the start button, and after the plunger has broken through the sample, press the stop button. Lower table and remove sample. To read the printer, with 500 my setting, the left is 0, middle is 250 and the right side is 500 for gel strength.

EXAMPLE

The following example was conducted: An egg mixture from egg breaking spinnings comprising 11.07% solids, 2.63% fat and 7.18% protein was passed through a membrane assembly comprising four loops with 32 vessels having a pore size of 0.2 um, at a base pressure of 3 psi and one loops at 8 psi boost and 3 loops at 7 psi boost, at a temperature of between 63 and 71 degrees and a flow rate of 18 gallons per minute and diafiltration water added at a rate of 2.5 gallons per minute. This configuration produced a permeate of 4.24% solids testing to 3.13% protein and 0.07% fat at a rate of 15.8 gallons per minute. The concentrate flow comprised 28.14% solids being 9.44% fat and 17.11% protein at a rate of 5 gallons per minute, indicating a yield of 38% of the available protein.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

This application is intended to cover adaptations or variations of the present subject matter. It is to be understood that the above description is intended to be illustrative, and not restrictive. It should be readily apparent that any one or more of the design features described herein may be used in any combination with any particular configuration. The scope of the present subject matter should be determined with reference to the appended claims, along with the full scope of equivalents to which such claims are entitled.

What is claimed is:

1. A method for separating proteins from an egg mixture, the method comprising:
    (a) obtaining an egg mixture comprising egg lipids and egg proteins; and
    (b) microfiltration of the egg mixture to obtain an isolated protein composition;
    wherein the microfiltration comprises pumping the egg mixture across a membrane with a pore size less than 0.40 microns at a pressure of less than 60 psi and the egg mixture is substantially free of egg-lipid cross-linking reagent.

2. The method for separating proteins from an egg mixture of claim 1, wherein the membrane comprises polyvinylidene fluoride.

3. The method of claim 1, wherein microfiltration comprises pumping the egg mixture across a spiral wound membrane.

4. The method of claim 1, wherein microfiltration comprises pumping the egg mixture across a filter with a pore size of equal to or less than 0.30 microns.

5. The method of claim 1, wherein microfiltration comprises pumping the egg mixture across a filter with a pore size of equal to or less than 0.20 microns at a pressure of less than about 30 psi.

6. The method for separating proteins from an egg mixture of claim 1, wherein the egg mixture comprises at least 1 percent egg lipid.

7. The method for separating proteins from an egg mixture of claim 1, wherein the egg mixture comprises at least 5 percent egg lipid.

8. The method of claim 1, wherein the membrane is constructed from a hydrophilic material.

9. The method of claim 1, wherein the pH of the mixture is not manipulated during separation.

10. The method of claim 1, wherein the egg mixture comprises inedible egg.

11. The method of claim 1, wherein the egg mixture comprises edible egg.

12. The method of claim 1, wherein the egg mixture comprises between about 40%-80% protein by dry weight and between about 35%-15% fat by dry weight before processing.

13. A method for separating proteins from an egg mixture, the method comprising:
    (a) obtaining an egg mixture comprising egg yolk lipids, egg yolk proteins, and egg albumen; and
    (b) microfiltration of the egg mixture comprising egg yolk lipids, egg yolk proteins, and egg albumen to obtain a isolated protein composition containing yolk-derived proteins and albumen-derived proteins;
    wherein the egg mixture is substantially free of egg-lipid crosslinking reagent; and
    wherein microfiltration comprises pumping the egg mixture across a membrane with a pore size of less than 0.5 microns at a pressure of less than 60 psi.

14. The method for separating proteins from an egg mixture of claim 13, wherein the egg mixture comprises at least 1 percent egg yolk lipid.

15. The method for separating proteins from an egg mixture of claim 13, wherein the egg mixture comprises at least 5 percent egg yolk lipid.

16. A method for separating proteins and lipids from an egg mixture, the method comprising:
    (a) obtaining an egg mixture comprising egg yolk lipids and egg yolk proteins; and
    (b) microfiltration of the egg mixture to separate the egg yolk lipids from the egg yolk proteins;

wherein the egg mixture is substantially free of egg-lipid crosslinking reagent and wherein the microfiltration comprises pumping the egg mixture across a membrane with a pore size of 0.4-0.05 microns at a pressure sufficiently low so as not to cause premature fouling of the membrane before the separation is complete.

17. The method for separating proteins from an egg mixture of claim 16, wherein the microfiltration comprises pumping the egg mixture across a membrane comprising polyvinylidene fluoride.

18. The method for separating proteins from an egg mixture of claim 16, wherein the egg mixture comprises at least 1 percent egg yolk lipid.

19. The method for separating proteins from an egg mixture of claim 16, wherein the egg mixture comprises inedible egg.

20. The method for separating proteins from an egg mixture of claim 16, wherein the egg mixture comprises between about 40%-80% protein by dry weight and between about 35%-15% fat by dry weight before processing.

* * * * *